(12) United States Patent
Onitsuka et al.

(10) Patent No.: US 6,206,935 B1
(45) Date of Patent: Mar. 27, 2001

(54) HAIR DYEING METHOD

(75) Inventors: Satoshi Onitsuka; Kazuhiro Okada; Hajime Miyabe, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/512,466

(22) Filed: Feb. 24, 2000

(30) Foreign Application Priority Data

Feb. 25, 1999 (JP) .................................................. 11-047411

(51) Int. Cl.[7] ...................................................... A61K 7/13
(52) U.S. Cl. ................................. 8/431; 8/405; 8/127.5; 8/930; 8/426; 8/101
(58) Field of Search ..................................... 8/405, 127.51, 8/930, 931, 426, 101, 107, 431

(56) References Cited

U.S. PATENT DOCUMENTS

| | | | | |
|---|---|---|---|---|
| 3,912,446 | * | 10/1975 | Zviak et al. | 8/10.1 |
| 3,931,912 | * | 1/1976 | Hsiung | 222/94 |
| 5,224,964 | * | 7/1993 | Shami | 8/405 |
| 5,958,084 | * | 9/1999 | Shabata et al. | 8/408 |

* cited by examiner

*Primary Examiner*—Yogendra Gupta
*Assistant Examiner*—Derrick G. Hamlin
(74) *Attorney, Agent, or Firm*—Oblon, Spivak, McClelland, Maier & Neustadt, P.C.

(57) ABSTRACT

Described in the present invention is a hair dyeing method comprising treating the hair with a hair bleaching agent and then, without rinsing off the bleaching agent, with a direct hair dye. The present invention makes it possible to color the hair into a vivid color in a short time.

10 Claims, No Drawings

HAIR DYEING METHOD

BACKGROUND OF THE INVENTION

1. Field of the Invention

The present invention relates to a hair dyeing method for dyeing the hair into a vivid color in a short time.

2. Description of the Related Art

A direct hair dye which colors the hair by allowing a direct dye such as acid dye to penetrate into the hair is most widely used, because it is safer and more convenient than an oxidative hair dye. A direct hair dye only adds color by allowing a direct dye to permeate into the hair so that the color available by dyeing depends on the color of the hair to be dyed. For the addition of a particularly vivid color to the hair, decoloring of the hair by bleaching in advance is very effective.

Since a bleaching agent is usually composed of an alkali agent and hydrogen peroxide, it is necessary to wash away the bleaching agent from the bleached hair and in most cases, to dry the hair prior to the treatment with a hair dye. Thus, vivid coloring of the hair with a direct hair dye is accompanied with the problem that the treatment is cumbersome and needs much time.

SUMMARY OF THE INVENTION

The present inventor has found that in spite that an alkali agent and hydrogen peroxide which have remained on the bleached hair are believed to adversely affect on the subsequent treatment with a direct dye unless they are rinsed away, the hair can be dyed into a vivid color by the treatment with a dye without rinsing them away.

In the present invention, there is thus provided a dyeing method comprising treating the hair with a hair bleaching agent and then, without washing the bleaching agent away, with a direct hair dye.

According to the present invention, the hair can be dyed into a vivid color in a short time.

DETAILED DESCRIPTION OF THE PREFERRED EMBODIMENTS

In the dyeing method of the present invention, usable is a popularly-used hair bleaching agent which decomposes melanin in the hair by the action of the alkali agent and oxidizing agent contained in the bleaching agent. Examples of the alkali agent include ammonia, monoethanolamine, diethanolamine, triethanolamine, isopropanolamine, propane-1,3-diamine, ammonium or alkali carbonates, ammonium or alkali bicarbonates, alkali silicates, alkali metasilicates, organic carbonates (ex. guanidine carbonate) and alkali hydroxides, and mixtures thereof. Examples of the oxidizing agent include hydrogen peroxide, alkali bromates, ammonium or alkali salts of peroxy acid (ex. potassium peroxodisulfate) and polythionates, and mixtures thereof.

A hair bleaching agent is formed of two parts to be mixed upon use. At least one of these two parts contains an alkali agent and it is in the solid or liquid form. After mixing, the composition may be in any desired form such as lotion which may optionally be thickened, cream or gel. In the hair bleaching agent, it is possible to incorporate, in addition to the above-described components, those ordinarily usable for the hair bleaching agent such as surfactant, cationic polymer, anionic polymer, nonionic polymer, oil component, perfume, antiseptic, silicone derivative, ultraviolet absorber, pH regulator, sequestering agent, antioxidant, bactericide and/or propellant. The hair bleaching agent is prepared in a conventional manner.

Treatment with such a hair bleaching agent is carried out, for example, by mixing upon use a first component containing ammonia as an alkali agent with a second component containing hydrogen peroxide as an oxidizing agent, applying the resulting mixture to the hair and then allowing it to stand for about 1 to 30 minutes. Bleaching effects can be heightened as needed by heating the hair by a heater or the like while it is allowed to stand after application.

In the dyeing method according to the present invention, the hair after bleaching is not washed prior to the treatment with a direct hair dye. Although the hair bleaching agent is not washed away, it is preferred to wipe off the excess with a towel or the like or to dry the hair by a hair drier or the like. As the direct hair dye, an acid hair dye relatively free from the hair damage is preferred.

As an acid hair dye, that containing (A) an acid dye and having a pH of 2 to 6 is preferred, with that further containing a solvent being more preferred and that containing (A) an acid dye and (B) an alkylene carbonate having 2 to 5 carbon atoms in total and having a pH of 2 to 6 being particularly preferred.

There is no particular limitation imposed on the nature of the acid dye used as component (A) of the acid hair dye insofar as it is water soluble. Examples include Red No. 120, Yellow No. 4, Yellow No. 5, Red No. 201, Red No. 227, Orange No. 205, Brown No. 201, Red No. 502, Red No. 503, Red No. 504, Red No. 506, Orange No. 402, Yellow No. 402, Yellow No. 406, Yellow No. 407, Red No. 213, Red No. 214, Red No. 3, Red No. 104, Red No. 105(1), Red No. 106, Green No. 2, Green No. 3, Orange No. 207, Yellow No. 202(1), Yellow No. 202(2), Blue No. 202, Blue No. 203, Blue No. 205, Blue No. 2, Yellow No. 203, Blue No. 201, Green No. 201, Blue No. 1, Red No. 230(1), Red No. 231, Red No. 232, Green No. 204, Green No. 205, Red No. 401, Yellow No. 403(1), Green No. 401, Green No. 402, Black No. 401 and Violet No. 401.

At least one of the above-exemplified acid dyes can be used. Incorporation of it in an amount of 0.2 to 5 wt.% (which will hereinafter be called %, simply), particularly 0.2 to 4%, still more preferably 0.2 to 3% based on the whole composition is preferred upon practical use, because it brings about sufficient dyeing effects and is relatively free from the staining of hands or skin.

Preferred examples of the component (B) used for the acid hair dye include ethylene carbonate and propylene carbonate, of which the propylene carbonate is particularly preferred.

The component (B) is preferably added to the acid hair dye in an amount of 0.5 to 50%, more preferably S to 50%, particularly preferably 10 to 35% from the viewpoints of the hair dyeing properties and prevention of skin coloring.

The acid hair dye is required to have pH 2 to 6, preferably 2 to 5, more preferably 2.5 to 4. At excessively low pH, the acid component presumably roughens the hair, scalp or hands, while at excessively high pH, penetration accelerating effects of the acid dye are lowered.

The pH can be adjusted by incorporating an organic acid or an inorganic acid, or a salt thereof having a buffering action within a pH range of 2 to 6. Examples of the organic acid include citric acid, glycolic acid, succinic acid, tartaric acid, lactic acid, fumaric acid, malic acid, levulinic acid, butyric acid, valeric acid, oxalic acid, maleic acid and mandelic acid. Examples of the inorganic acid include phosphoric acid, sulfuric acid and nitric acid. Examples of the salt of such an acid include sodium salts, potassium salts, ammonium salts and alkanolamine salts, e.g., triethanolamine salt.

For the purpose of improving the dyeing properties of the acid hair dye, it is possible to add thereto at least one organic solvent, as component (C), selected from benzyloxyethanol, benzyl alcohol, phenoxyethanol, phenoxyisopropanol, benzyl glycerol, N-benzylformamide, cinnamyl alcohol, phenetyl alcohol, p-anisyl alcohol, p-methylbenzyl alcohol, methyl carbitol, ethyl carbitol and propyl carbitol. As the organic solvent serving as component (C), aromatic alcohol analogues are preferred, of which the benzyloxyethanol and benzyl alcohol are particularly preferred. In consideration of the effects for improving the dyeing properties and preventing the coloring of the skin, it is preferred to add the component (C) in an amount of 0 to 10%, preferably 0.01 to 10%, particularly preferably 0.1 to 5%, to the acid hair dye.

In the acid hair dye, a water-soluble high molecule (D) can be incorporated in order to prevent the dripping of it upon use and staining of the scalp with it. Examples of the water-soluble high molecules include arabic gum, carrageenan, karaya gum, tragacanth gum, carob gum, quince seed, casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinyl methyl ether (PVM), polyvinyl pyrrolidone (PVP), sodium polyacrylate, locust bean gum, guar gum, tamarind gum, dialkyldimethylammonium sulfate cellulose, xanthan gum, modified xanthan gum, magnesium aluminum silicate and bentonite. Among them, hydroxyethyl cellulose, xanthan gum and modified xanthan gum are particularly preferred.

As the water-soluble high-molecule, at least one of the above-exemplified ones can be employed. It is preferably added in an amount of 0.1 to 10%, particularly 0.5 to 5% to the acid hair dye.

To the acid hair dye, a lower alcohol or polyol can also be added in order to heighten the solubility of the components (B) and (D). Specific examples include $C_{2-4}$ alcohols or polyols such as ethanol, isopropanol, n-propanol, n-butanol, ethylene glycol, propylene glycol, isopropylene glycol, 1,3-butylene glycol and glycerin. At least one of these lower alcohols or polyols can be used. It is preferably added in an amount of 0.1 to 30%, particularly 0.1 to 20% to the acid hair dye.

Moreover, additives ordinarily used for cosmetics such as surfactant, cationic polymer, oily component, silicone derivative, perfume, antiseptic, ultraviolet absorber, antioxidant, bactericide and/or propellant can be added to the acid hair dye in an amount within an extent not impairing the advantages of the present invention. The acid hair dye can be prepared in a conventional manner.

The direct hair dye is applied to the hair, for example, by putting a proper amount of it on a comb or brush, applying it to the hair, allowing it to stand for 1 to 30 minutes after application and then washing it away. Heat treatment, for example, by a heater after application of the direct hair dye but before washing is more preferred. Heating is preferably carried out so that the temperature around the surface of the hair would become 40 to 50° C.

EXAMPLES

The hair was dyed in accordance with the following procedures by using a hair bleaching agent shown in Table 1 and a direct hair dye shown in Table 2.

TABLE 1

| Hair bleaching agent | A | B | (wt. %) C |
|---|---|---|---|
| (First component) | | | |
| Aqueous ammonia (28%) | 3.0 | 3.0 | — |
| Monoethanolamine | 2.5 | 2.5 | — |
| Cetyl alcohol | 5.0 | 5.0 | — |
| Stearic acid | 2.0 | 2.0 | — |
| Hydroxyethylcellulose dimethylallylammonium chloride | 0.8 | 0.8 | — |
| Polyoxyethylene (21) lauryl ether | 5.0 | 5.0 | — |
| Polyoxyethylene (5) cetyl ether | 5.0 | 5.0 | — |
| Sodium cetylsulfate | 2.0 | 2.0 | — |
| Vaseline | 5.0 | 5.0 | — |
| Propylene glycol | 3.0 | 3.0 | — |
| Sodium sulfite | 0.1 | 0.1 | — |
| Ammonium sulfate | 0.2 | 0.2 | — |
| Potassium peroxodisulfate | — | — | 35.0 |
| Sodium peroxodisulfate | — | — | 15.0 |
| Sodium silicate | — | — | 15.0 |
| Sodium metasilicate | — | — | 10.0 |
| Sodium stearate | — | — | 5.0 |
| Silica | — | — | 10.0 |
| Ammonium chloride | 1.5 | — | 5.0 |
| Hydroxyethyl cellulose | — | — | 4.0 |
| EDTA | — | — | 1.0 |
| Purified water | Balance | Balance | — |
| (Second component) | | | |
| Hydrogen peroxide (35%) | 17.0 | 17.0 | 17.0 |
| Cetanol | 2.0 | 2.0 | 2.0 |
| Sodium laurylsulfate | 0.5 | 0.5 | 0.5 |
| Phosphoric acid | 0.02 | 0.02 | 0.02 |
| EDTA | 0.5 | 0.5 | 0.5 |
| Purified water | Balance | Balance | Balance |
| (Third component) | | | |
| Potassium peroxodisulfate | — | 50.0 | — |
| Sodium peroxodisulfate | — | 45.0 | — |
| Silica | — | 5.0 | — |

TABLE 2

| Direct hair dye | X | Y | (wt. %) Z |
|---|---|---|---|
| Orange No. 205 | 0.33 | 0.32 | 0.33 |
| Violet No. 401 | 0.03 | 0.09 | 0.03 |
| Red No. 106 | 0.11 | — | 0.11 |
| Black No. 401 | — | 0.03 | — |
| Propylene carbonate | 16.0 | 16.0 | 15.0 |
| Benzyloxyethanol | — | — | 2.5 |
| Ethanol | 4.0 | 4.0 | 7.0 |
| Lactic acid | 4.5 | 4.5 | 8.0 |
| Sodium hydroxide | Adjusted to pH 2.9 | Adjusted to pH 2.9 | Adjusted to pH 2.9 |
| Xanthan gum | 1.2 | 1.2 | 1.2 |
| Purified water | Balance | Balance | Balance |

The hair used hereinafter in Examples and Comparative Examples is a hair bundle prepared for evaluation by using untreated hair of one bundle prepared for evaluation by using a weight of 10g.

Example 1

(1) The first and second components of a hair bleaching agent A were mixed at a weight ratio of 1:1. The resulting mixture was applied to the hair and allowed to stand for 15 minutes. (2) A direct hair dye Z was then applied and allowed to stand for 15 minutes after application. (3) The agents were both rinsed off with warm water and the hair was shampooed. After drying with a towel, the hair was dried by a drier.

Comparative Example 1

Between the operations (1) and (2) of Example 1, the following operation (a) was inserted. (a) After the hair bleaching agent was rinsed off with warm water, the hair was shampooed, dried with a towel and then dried by a drier.

Example 2

(1) The first, second and third components of a hair bleaching agent B were mixed at a weight ratio of 1:1:0.1. The resulting mixture was applied to the hair and allowed to stand for 10 minutes. (2) A direct hair dye Y was then applied to the hair and allowed to stand for 15 minutes after application. (3) After both of the agents were rinsed off with warm water, the hair was shampooed, dried with a towel and then dried by a drier.

Comparative Example 2

Between the operations (1) and (2) of Example 2, the above-described operation (a) of Comparative Example 1 was inserted.

Example 3

(1) The first and second components of a hair bleaching agent C were mixed at a weight ratio of 1:2. The resulting mixture was applied to the hair and allowed to stand for 10 minutes. (2) The excess of the hair bleaching agent on the hair was wiped off with a towel. (3) A direct hair dye X was then applied and allowed to stand for 5 minutes after application while heating so that the temperature around the surface of the hair would become about 50°C. (3) After both of the agents were rinsed off with warm water, the hair was shampooed, dried with a towel and then dried by a drier.

Comparative Example 3

Between the above-described operations (2) and (3) of Example 3, the above-described operation (a) of Comparative Example 1 was inserted.

The hair dyeing properties were compared between Example 1 and Comparative Example 1, Example 2 and Comparative Example 2 and Example 3 and Comparative Example 3, respectively. The results are shown in Table 3. The hair bundles treated in accordance with the operations of Example and Comparative Example, respectively were visually compared and evaluated by a panel of 10 experts. (Ranking standards)

A: The hair was dyed better in Example than in Comparative Example.

B: The dyed degree was almost similar between Example and Comparative Example.

C: The hair was dyed better in Comparative Example than Example.

| Example | 1 | 2 | 3 |
|---|---|---|---|
| Comparative Example | 1 | 2 | 3 |
| who made A-ranking | 0 | 0 | 0 |

-continued

| Example | 1 | 2 | 3 |
|---|---|---|---|
| Comparative Example | 1 | 2 | 3 |
| who made B-ranking | 10 | 10 | 10 |
| who made C-ranking | 0 | 0 | 0 |

From the results of Table 3, it has been found that deterioration of dying properties does not occur even without washing after bleaching treatment, which makes it possible to dye the hair conveniently in a reduced operation time.

What is claimed is:

1. A hair dyeing method, which comprises treating the hair with a hair bleaching agent and then, without washing away said bleaching agent, treating the hair with a direct hair dye, wherein the direct hair dye contains an acid dye (A), and propylene carbonate (B) and/or at least one organic solvent (C) selected from the group consisting of benzyloxyethanol, benzyl alcohol, phenoxyethanol, phenoxyisopropanol, benzyl glycerol, N-benzylformamide, cinnamyl alcohol, phenetyl alcohol, panisyl alcohol, p-methylbenzyl alcohol, methyl carbitol, ethyl carbitol and propyl carbitol, and has a pH of 2 to 6.

2. A method according to claim 1, which further comprises heating the hair after treatment with the hair bleaching agent and/or direct hair dye.

3. A method according to claim 1, wherein the direct hair dye contains said propylene carbonate.

4. A method according to claim 1, wherein the direct hair dye contains the organic solvent (C).

5. A method according to claim 4, wherein the organic solvent contains benzyloxyethanol or benzyl alcohol.

6. A method according to claim 4, wherein the direct hair dye contains 0.01 to 10% of the organic solvent (C).

7. A method according to claim 1, wherein the direct hair dye has a pH of 2 to 5.

8. A method according to claim 1, wherein the direct hair dye has a pH of 2.5 to 4.

9. A method according to claim 1, wherein the direct hair additionally contains at least one component (D) selected from the group consisting of arabic gum, carrageenan, karaya gum, tragacanth gum, carob gum, quince seed, casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinyl methyl ether (PVM), polyvinyl pyrrolidone (PVP), sodium polyacrylate, locust bean gum, guar gum, tamarind gum, dialkyldimethylammonium sulfate cellulose, xanthan gum, modified xanthan gum, magnesium aluminum silicate and bentonite.

10. The method of claim 9, wherein the component (D) is hydroxyethyl cellulose, xanthan gum or modified xanthan gum.

* * * * *